United States Patent [19]

Schenck et al.

[11] Patent Number: 5,431,620
[45] Date of Patent: Jul. 11, 1995

[54] METHOD AND SYSTEM FOR ADJUSTING CENTRIFUGE OPERATION PARAMETERS BASED UPON WINDAGE

[75] Inventors: Alan L. Schenck, Sunnyvale; Jin Y. Song, Saratoga, both of Calif.

[73] Assignee: Beckman Instruments, Inc., Fullerton, Calif.

[21] Appl. No.: 271,860

[22] Filed: Jul. 7, 1994

[51] Int. Cl.⁶ .................................................. B04B 13/00
[52] U.S. Cl. ................................................ 494/7; 494/10; 494/14; 494/37; 494/61; 210/145; 210/739; 210/787
[58] Field of Search .................. 494/1, 7, 8, 9, 10, 494/11, 12, 13, 14, 16, 37, 61, 84; 422/72, 105, 108; 436/45; 210/145, 739, 774, 787, 808

[56] References Cited

U.S. PATENT DOCUMENTS

| | | | |
|---|---|---|---|
| 3,409,212 | 11/1968 | Durland et al. | 494/16 X |
| 4,449,965 | 5/1984 | Strain | 494/16 |
| 4,451,248 | 5/1984 | Williams | 494/84 |
| 4,509,940 | 4/1985 | Romanauskas | 494/16 |
| 4,693,702 | 9/1987 | Carson et al. | 494/84 X |
| 4,827,197 | 5/1989 | Giebeler | 494/10 X |
| 4,857,811 | 8/1989 | Barrett et al. | 318/3 |
| 5,171,206 | 12/1992 | Marque | 494/37 |
| 5,235,864 | 8/1993 | Rosselli et al. | 494/10 X |

FOREIGN PATENT DOCUMENTS 3632087  7/1987  Germany .................. 494/10

*Primary Examiner*—Charles E. Cooley
*Attorney, Agent, or Firm*—William H. May; Gary T. Hampson; Schneck & McHugh

[57] ABSTRACT

A method and system of determining an operation parameter for a centrifuge includes measuring one or more physical characteristics of a rotor interchangeably supported by a rotor drive. In the preferred embodiment, windage is measured at a first rotational speed and a speed-dependent signal is generated to adjust a vacuum system based upon changes in rotational speed of the rotor. Changes in windage may also be used as a basis for adjusting a refrigeration circuit. Either as an alternative or in addition to monitoring windage, the moment of inertia can be measured and used to adjust adaptive circuitry. For example, the drive circuitry may be adjusted based upon a determination of inertia as the physical characteristic of interest. The method and system isolate inertia and windage as the main forms of resistance to acceleration of the rotor.

18 Claims, 2 Drawing Sheets

METHOD AND SYSTEM FOR ADJUSTING CENTRIFUGE OPERATION PARAMETERS BASED UPON WINDAGE

TECHNICAL FIELD

The invention relates generally to centrifuge systems and more particularly to methods and systems for determining process parameters of a centrifugal operation.

BACKGROUND ART

Centrifuge systems are routinely used to separate a biological or chemical sample into components of the sample. The sample is supported within a centrifuge rotor that is driven at a velocity to cause the components to separate according to molecular weight.

While some heating of a centrifuge rotor occurs as a result of thermal conduction from a drive motor to the motor via a drive shaft, in most applications rotor heating occurs primarily by thermal conduction from the air or other gas within the chamber, with the gas being heated by the work done on the gas by the rotor. This work takes the form of accelerating the gas and inducing a pumping action that then leads to rapid recirculation of the gas and a buildup of heat. "Windage" is primarily the power consumed in pumping the gaseous atmosphere surrounding the rotor. At high speeds, viscous frictional drag plays the role of providing mechanical coupling of the rotor to the mass of gas, resulting in the gas pumping. Thus, windage is distinguishable from inertial drag, which is dependent upon the mass and radial distribution of the rotor.

In addition to causing rotor heating, windage imposes a limitation on the maximum speed that can be achieved by a given drive motor. One approach to reducing windage is to enclose the rotor in a chamber and at least partially evacuate the chamber. Windage power varies with the mass of the gas within the chamber, the dimensions of the rotor, and the rotational speed of the rotor. The evacuation of gas within the chamber reduces the adverse effect of windage on accelerating the rotor, but has mixed results on allowing temperature control. While a reduction in generation of thermal energy follows from the evacuation of gas, a partially evacuated environment causes the thermal energy that is generated to remain localized about the rotor. It is known to use refrigeration coils around the exterior of the housing that forms the chamber, but the heat must be transferred from the rotor to the housing in order for the refrigeration system to provide the desired cooling. The evacuation renders convection heat transfer from the rotor to the housing less effective, so that a greater reliance is placed on heat transfer by irradiation.

Operating a vacuum system at a level in which the chamber is fully evacuated is often viewed as being undesirable. The required vacuum system is expensive. Moreover, fully evacuating the chamber greatly increases the evaporation rate of sample solution, thereby adversely affecting the analytical procedure, particularly for applications in which a rotor and specimen tubes remain open to the evacuated chamber.

U.S. Pat. No. 4,857,811 to Barrett et al. describes a centrifuge in which identification of a rotor within a centrifuge is used to control vacuum. Upon identification of the rotor, information regarding the identified rotor is extracted from a look-up table of data related to various rotors that may be operated with the centrifuge. A vacuum system is controlled in accordance with the information. Optionally, the rotational speed of the rotor can be monitored and the vacuum level can be changed with changes in speed.

One difficulty with an approach such as the one taken by Barrett et al. is that the vacuum control is memory intensive. Data must be stored for each possible rotor. Another difficulty is that the memory must be upgraded with each addition of a rotor compatible with the centrifuge system.

Optimum operation of the vacuum system and/or the refrigeration system of a centrifuge will vary based upon the rotor in use. This dependence of optional settings upon the rotor in use also applies to other process parameters. For example, optimal drive proportional and integral gain values for a centrifuge drive system will vary according to the inertia of the rotor. A feedback loop control for a drive system should utilize values that preferably are adjusted when a rotor is substituted with a rotor having a different inertia.

It is an object of the present invention to provide a centrifuge system and method which is adaptive to substitutions of rotors without requiring the adaptive circuitry to maintain data regarding each possible rotor available for use with the centrifuge system.

SUMMARY OF THE INVENTION

The above object has been met by a centrifuge system and method that adapt operation parameters based upon physical characteristics of rotors in use, rather than upon proper identification of the rotors. The physical characteristics of the rotor of interest are those that contribute to the resistance of the rotor to acceleration.

In the preferred embodiment, the windage resulting from rotating the rotor at a first rotational speed or relative to a first acceleration is ascertained and a signal based upon both the measured windage and the rotor speed is generated. The signal is referred to herein as a "speed-dependent windage signal." The speed-dependent windage signal may be then utilized to control a vacuum system. For example, a windage coefficient can be established based upon the windage measurement at the first speed and, by extrapolating the data, the windage coefficient can then be used to select a desired vacuum level at the eventual speed which the rotor is to reach. In a least complex form, the windage coefficient is a ratio of windage to speed. From the original determination of windage to speed, the eventual speed can be substituted for the speed at which windage was measured and, since windage increases with the cube of increases in speed, a measure of expected windage at the eventual speed can be estimated. The vacuum system can then be set according to the measure of expected windage.

Optionally, the speed-dependent signal may be used to provide dynamic control of a centrifuge run. Vacuum pressure can be varied in response to changes in windage. For this dynamic control, it is possible to periodically or continuously track windage directly or to monitor rotational speed and extrapolate from data obtained in generating the original speed-dependent windage signal, e.g. using the windage coefficient to determine changes in vacuum pressure. Typically, the vacuum level is increased with increases in rotational speed. However, the increases need not be proportional. Triggering an increase in vacuum level may be dependent upon windage exceeding a predetermined value.

With an increase in the vacuum level, the air mass within a centrifuge chamber is reduced. Consequently, both frictional drag and the work necessary to pump the air mass are reduced, thereby decreasing generation of thermal energy within the chamber. In addition to controlling vacuum level, or as an alternative to controlling vacuum, the speed-dependent windage signal may be used to control a refrigeration system of a centrifuge. Typically, the refrigeration system includes a thermistor or other temperature monitoring device located at the bottom of the enclosed chamber in which the rotor is spun. Since heat is generated by the rotation of the rotor, the temperature is greater near the rotor than it is at the thermistor. In prior art centrifuges, based upon this difference temperature, compensation values are established in order to more reliably maintain the rotor at a desired temperature. In one embodiment of the present invention, a temperature compensation value for the refrigeration system is determined by measuring windage at a preselected speed. If the rotor of interest exhibits high windage characteristics at the preselected speed, the compensation value is set higher, e.g., $\Delta$ temperature = 12° C., than if the rotor exhibits low windage characteristics. The compensation value may be fixed throughout a particular centrifuge run, or the refrigeration system can be controlled dynamically to change the value with changes in speed.

At high speeds, windage is the primary factor in total resistance of the rotor to acceleration. However, inertia also plays a role. In the preferred embodiment, determining windage includes discounting inertia.

Alternatively, the measure of resistance of the rotor to acceleration is a measure of inertia at low speeds. The measure of inertia may then be used to adjust drive proportional and integral gain values for feedback loop control of a centrifuge drive system. If the values were not adjusted whenever a first rotor was replaced with a second rotor having a different inertia, operation of the centrifuge with respect to acceleration and speed control would vary with the change in rotors. The invention allows the centrifuge drive system to "adapt" to the different rotors, as well as other factors and operating conditions that alter the inertia of the rotating assembly.

An advantage of the invention is that the adaptive circuitry is not memory-intensive. That is, the system and method may be utilized without a look-up table that stores desired relationships between each possible rotor and each operation parameter which is to be controlled in accordance with the selection of a rotor. Another advantage is that newly available rotors may be used with the adaptive circuitry, since no software update is required. Yet another advantage is that adjustments to the drive proportional and integral gain values, as well as other circuitry in which inertia dictates the adjustments, are made in accordance with changes in the volume of specimen of interest contained within a rotor.

BEST MODE FOR CARRYING OUT THE INVENTION

Figure 1:
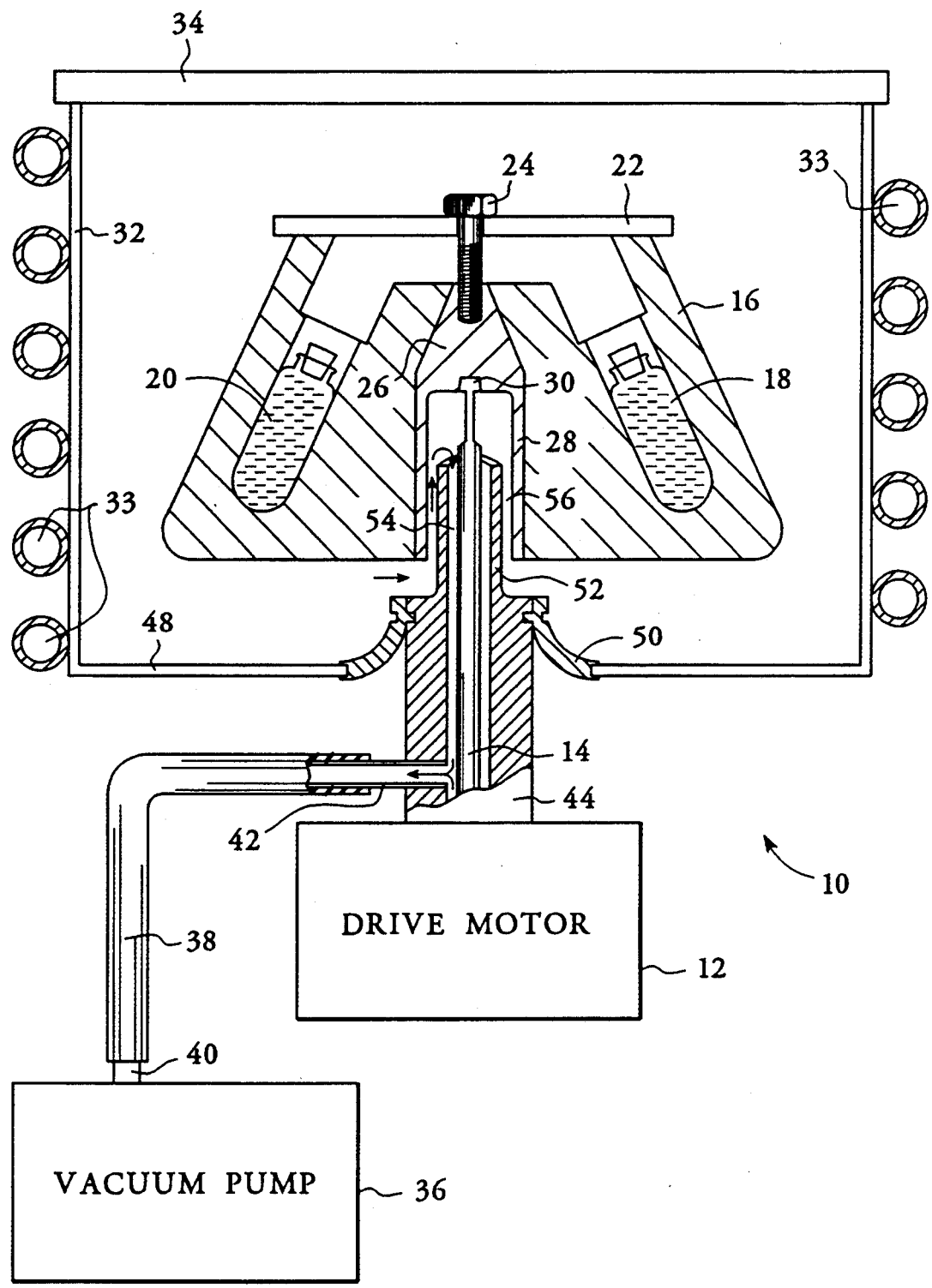
FIG. 1 is a side sectional view of a centrifuge for adaptive control in accordance with the present invention.

With reference to FIG. 1, a centrifuge 10 includes a drive motor 12 for rotating a drive shaft 14. While not critical, the drive motor may be a switched reluctance motor. An advantage of such a motor is that a readout of torque generated by the motor is available at all times. As will be explained more fully below, the monitoring of torque can be used to readily determine windage torque generated when a rotor 16 is driven by the motor 12.

The rotor 16 is shown as having compartments for securing at least two specimen containers 18 and 20 for the centrifugal separation of components of a sample within the containers. The containers 18 and 20 are placed in the rotor by removing a rotor lid 22. A bolt 4 extends through the hole in the rotor lid and is received within an internally threaded bore of a hub 26. The bolt secures the rotor lid to the rotor and secures the rotor to the hub.

The hub 26 is adapted for connection to any of a variety of models of rotors. The hub has a cylindrical, downwardly depending skirt 28. The hub is fixed to the upper end of the drive shaft 14 such that the cylindrical skirt is coaxial to the drive shaft. The rotational drive of the motor 12 is transferred to the rotor 16 by means of the drive shaft 14 and the hub 26. The upper end 30 of the drive shaft may be secured to the hub using conventional techniques. The rotor has an internal surface configured to receive the hub 26.

The rotor 16, the hub 26 and the upper portion 30 of the drive shaft 14 are contained within a chamber defined by a housing 32 having a cover 34. While not shown, typically vacuum seals are located at the interface of the cover with the remainder of the housing. The side walls and the bottom wall of the housing 32 may be a metallic framework having refrigeration coils 33 at external surfaces to control the temperature within the enclosed chamber defined by the housing.

In addition to temperature control, the atmosphere within the enclosed chamber of the housing 32 may be controlled by operation of a vacuum pump 36. A conduit 38 is connected to a fitting 40 that extends from the vacuum pump. At the opposite end of the conduit, the conduit is frictionally fit to a fitting 42 of a sleeve 44. The sleeve 44 has a lower, large diameter portion that extends coaxially with the drive shaft 14 to penetrate openings in the outer framework 46 and the bottom wall 48 of the housing 32. A vacuum seal 50 is connected at the bottom wall to the sleeve 44 to prevent leakage of air into the enclosed chamber of housing 32 after the evacuation of air from the housing.

A reduced diameter portion 52 of the sleeve 44 extends into the downwardly depending skirt 28 of the hub 26. Thus, a first annular gap 54 is formed between the drive shaft 14 and the upper surface of the sleeve 44. A second annular gap 56 is formed between the downwardly depending skirt 28 of the hub and the outside diameter of the portion 52 of the sleeve 44.

Air evacuation from the centrifuge chamber is upwardly into the second annular gap 56 and then downwardly into the first annular gap 54, whereafter evacuated air is channeled to the vacuum pump 36. As shown in FIG. 1, the motor 12 is also evacuated.

Figure 2:
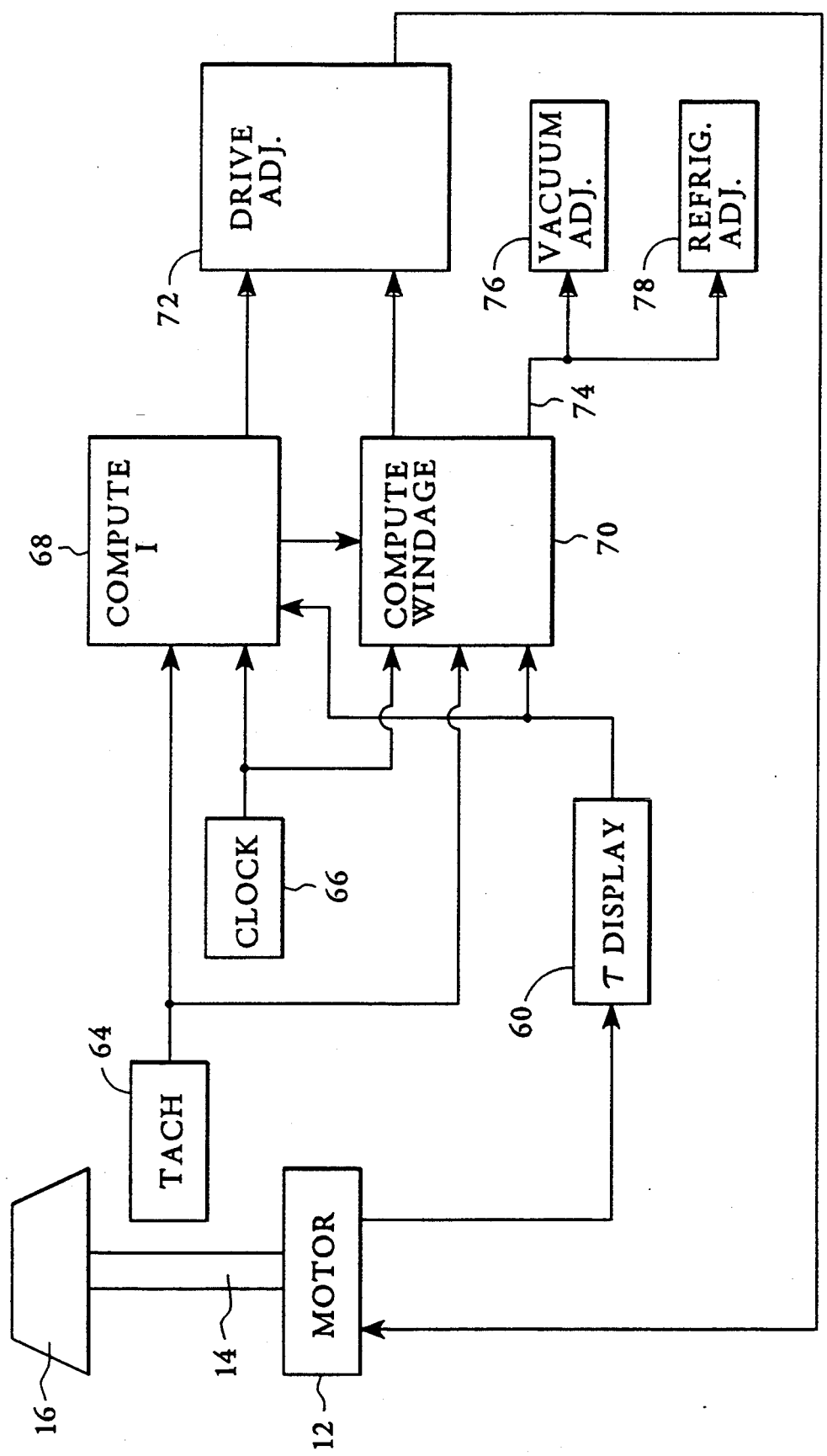
FIG. 2 is a block diagram of adaptive circuitry for the centrifuge of FIG. 1.

Referring now to FIG. 2, the drive motor 12 for rotating the rotor 16 via the drive shaft 14 is shown as including a torque display 60. As previously noted, the motor 12 preferably is one which monitors torque input to the rotating structure, so that determining windage is facilitated.

The system of FIG. 2 includes a tachometer 64 and a clock 66, with each providing an input to circuitry 68 for computing inertia and circuitry 70 for computing windage. Inertia and windage are the main factors in the resistance of the rotor 16 to acceleration by the motor 12. Inertia plays a larger role at relatively low rotational speeds, since windage torque increases exponentially with increases in speed. However, inertia plays a significant role in determining the total resistance to acceleration even at high speeds. Inertia is a function of the mass of the rotor 16 and its radial distribution. The windage of a particular rotor varies as the rotational speed cubed, the rotor diameter to the fifth power and the length slightly less than directly.

The moment of inertia of the rotor can be determined using the equation as follows:

$$I = \frac{\tau}{\alpha},$$

where $\tau$ is the torque and e is the angular acceleration. Because the preferred embodiment includes a readout of torque from the display 60, the moment of inertia can be determined by performing a timed acceleration in a manner to be described below. Torque can be calculated from the electrical current input to the motor 12 or by using other known techniques. Alternatively, the calculation of inertia can be performed with the motor input torque maintained at the same fixed value for all instances in which inertia is at issue, so that the inertia circuitry can merely utilize the fixed torque value for all such calculations. Utilizing this last alterative, the connection between circuitry 68 and motor 12 would not be necessary.

Angular acceleration ($\alpha$) can be measured using values from a timed acceleration, either measuring a time period ($\Delta t$) necessary for acceleration ($\Delta \omega$) from a first rotational speed to a selected second rotational speed, or measuring the change in speed ($\Delta \omega$) within a set time ($\Delta t$) period. The angular acceleration can then be determined using the equation:

$$\alpha = \frac{\Delta \omega}{\Delta t}.$$

The speed of rotor 16 is monitored using the tachometer 64. Tachometers and equivalent devices are conventionally used in centrifuge systems. The clock 66 is also utilized in the timed acceleration of the rotor 16. Thus, the inertia computation circuit 68 receives an input from the tachometer 64 and the clock 66 to compute $\Delta \omega$ and $\Delta t$ for the timed acceleration of the rotor 16.

Based upon the values of $\Delta \omega$ and $\Delta t$ during the timed acceleration, the angular acceleration ($\alpha$) is calculated. In its least complex form, the input torque of the motor 12 is held constant, so that the moment of inertia is merely a division of the computed angular acceleration into the value of torque. However, persons skilled in the art will readily understand that the moment of inertia can be calculated for timed accelerations in which torque is not held constant.

Based upon the computation of the moment of inertia at circuitry 68, adjustments can be made to adaptive circuitry of the centrifuge system. For example, FIG. 2 shows the inertia computation circuitry 68 as providing an input to drive adjust circuitry 72. The drive adjust circuitry 72 may be circuitry having variable values for proportional gain and integral gain. Thus, an adjustable feedback loop control system is created. The drive is stabilized by tailoring the pertinent values based upon calculated inertia.

Adjustments to the circuitry 72 are dependent directly on a physical characteristic of the rotor 16. That is, rotor identification is not required. An advantage of this approach is that newly available rotors may be used without updating a look-up table to include properly tailored drive proportional and integral gain values. Another advantage is that more precise tailoring of the values can be provided even if a single rotor is utilized. A rotor has a minimum inertia value and a maximum inertia value. Within the range defined by the two inertia values, the moment of inertia for a particular centrifugal operation will vary according to the quantity of specimen contained within the rotor during the operation. Since the adaptive circuitry of FIG. 2 is dependent upon the physical characteristic of inertia and not upon identification of a rotor, the adjustments can be based upon actual inertia, rather than upon some value of inertia within the range of values associated with an identified rotor.

The circuitry 70 for computing windage includes inputs from the torque display 60, the tachometer 64 and a clock 66. As previously noted, the drive motor 12 is preferably a switched reluctance motor. Switched reluctance drives provide precise torque data that are available in realtime on a continuous basis from drive control electronics. Consequently, the torque display is not a necessary element of the invention. Furthermore, a switched reluctance drive has a continuously operating armature-position indicator that is required for proper operation of the motor. The frequency of pulses from the armature-position indicator may be used to determine the rotational speed of the rotor 16, so that the tachometer 64 is not a necessary element of the centrifuge system. The computation of inertia at circuitry 68 is performed at relatively low speeds in which windage is negligible, and ideally nonexistent. The first selected speed from which the rotor 16 is accelerated may be 0 rpm.

In comparison, the measurement of windage power at circuitry 70 should be performed at relatively high speeds. The least complex computation of windage is one in which the rotor 16 is maintained at a constant high speed by the switched reluctance motor 12 and information that is available directly from the motor is utilized. At a selected high constant speed, the torque input, adjusted for known motor losses, is substantially equal to windage power, i.e., air pumping power. At the high constant speed, the inertial drag of the rotor is 0.

In another embodiment, the computation of windage at circuitry 70 is based upon a second measured acceleration. Again, either the time period ($\Delta t$) or the incremental increase in rotational speed ($\Delta \omega$) may be preselected, with the other factor being measured. Windage power is then calculated to be the difference between torque input ($\tau$) and the product of the moment of inertia (I) times the change in rotational speed ($\Delta \omega$) divided by the change in time ($\Delta t$), i.e., windage = $\tau - I (\Delta \omega / \Delta t)$.

The measure of windage at circuitry 70 is used to establish a speed-dependent windage value. For example, a windage coefficient may be a ratio of the measurement of windage to a speed indicated by tachometer 64 at the time of measuring windage. The speed, or range of speeds, at which windage is measured is typically less than the previously selected maximum speed that the rotor is to eventually reach. The windage coefficient is used to extrapolate the expected windage at the selected maximum speed. Windage is considered to increase to the cube of increases in rotational speed, so that the extrapolation preferably, but not critically, factors this relationship into the extrapolation. Based upon the extrapolated value of windage, the drive adjust circuitry 72, a vacuum adjust circuit 76, and/or a refrigeration adjust circuit 78 can be controlled. Input/output line 74 is shown as providing a speed-dependent windage signal to the vacuum adjust circuit and the refrigeration adjust circuit.

Referring specifically to the vacuum adjustment at circuit 76, the speed-dependent windage signal from the input/output line 74 may be used to set the level of vacuum pressure according to expected windage at a selected maximum speed. Unlike prior art vacuum offset circuits, the adjustment is not dependent upon proper identification of the rotor 16. Since windage will vary with the cube of changes to rotational speed, adjustments to vacuum may be easily computed. The determination may merely be one of whether to activate or leave inactive the vacuum system. However, dynamic vacuum control is also possible.

Conventionally, the temperature of the rotor 16 is monitored by locating a thermistor at the bottom wall of the chamber in which the rotor is housed. The difference in temperature at the rotor relative to the thermistor must be considered. Since the thermal energy is generated primarily at the rotor as a result of fluid friction, the temperature of the rotor will be higher than the temperature at the thermistor. For example, the rotor temperature may be 4° C. greater than the temperature sensed by the thermistor. Consequently, it is known to use a compensation value to offset this temperature differential. The compensation value should be greater for rotors in high windage conditions than for rotors in low windage conditions. The system of FIG. 2 can be used to establish a compensation value for an unknown rotor.

Since an increase in vacuum will affect the conduction of thermal energy from the rotor to the thermistor and to the refrigeration coils of the centrifuge, the temperature differential between the rotor and the thermistor will also change with changes in the vacuum level. Optionally, the speed-dependent windage signal along line 74 may be used to simultaneously adjust the vacuum level at circuit 76 and adjust the temperature compensation value at circuit 78 to reflect the change in vacuum level. For example, as vacuum is increased, the compensation value representative of the rotor/thermistor temperature differential may be increased at circuit 78.

Using the system of FIG. 2, a vacuum level can be selected to optimize a centrifuge run in terms of windage losses, rotor set speed, rotor heating and overall power input to the drive motor 12. This can be done without dependence upon extensive look-up tables in software to provide desired run parameters for each rotor that may be used with the centrifuge system. Laboratory centrifuges are typically adapted to interchangeably receive a variety of rotor models. Basing the adjustments of vacuum and refrigeration upon one or more measured physical characteristics of a rotor of interest, rather than upon rotor identification, allows the system to be less dependent upon computer memory. Moreover, newly available rotors may be utilized with the system without requiring an update to computer memory.

The invention claimed is:

1. A method of selectively varying an operation parameter for a centrifuge comprising:
   rotating a centrifuge rotor at a first rotational speed;
   determining resistance of said centrifuge rotor to said rotating;
   determining a relationship between said resistance and said operation parameter;
   selecting a second rotational speed greater than said first rotational speed;
   determining a predicted operating value of said operation parameter at said second rotational speed, including extrapolating from said relationship in order to obtain said predicted operating value; and
   setting said operation parameter to said predicted operating value for a centrifuge run in which said centrifuge rotor is accelerated to said second rotational speed.

2. The method of claim 1 wherein said determining said resistance to rotating is a step including measuring windage at said first rotational speed of said centrifuge rotor.

3. The method of claim 2 wherein said extrapolating includes basing an expectation of windage at said second rotational speed upon said measuring windage at said first rotational speed and further includes estimating said predicted operating value in response to said expectation of windage at said second rotational speed.

4. The method of claim 3 wherein said setting said operation parameter includes controlling a source of vacuum such that vacuum pressure within said centrifuge is selected in response to said expectation of windage at said second rotational speed.

5. The method of claim 3 wherein said setting said operation parameter includes controlling a source of refrigeration such that a temperature compensation value is set in accordance with an expected temperature difference between said centrifuge rotor and a device for measuring temperature.

6. The method of claim 3 wherein said measuring windage includes isolating effects of windage from inertia as a source of resistance of said centrifuge rotor to said rotating.

7. The method of claim 1 wherein said determining resistance to rotating includes measuring inertia, said setting said operation parameter being a step of adjusting one of drive proportional and integral gain values for a drive system of said centrifuge.

8. A method of operating a centrifuge during a centrifugal separation comprising:
   ascertaining windage of a centrifuge rotor when said rotor is spun at a first rotational speed;
   generating a windage signal responsive to said ascertaining windage;
   based upon said windage signal, forming an estimation of windage of said rotor at a second rotational speed;
   identifying a desired relationship between said estimation of windage and a selected operating condition for said centrifugal separation; and
   controlling said centrifuge in a manner such that said desired relationship is promoted.

9. The method of claim 8 wherein said generating said windage signal includes calculating a windage coefficient based upon values of said first rotational speed and said windage at said first rotational speed.

10. The method of claim 8 further comprising determining inertia of said centrifuge rotor and adjusting one of drive proportional and integral gain values for a drive system of said centrifuge.

11. The method of claim 8 wherein said identifying said desired relationship is a step including establishing a relationship between vacuum pressure within said centrifuge and said estimation of windage, said controlling said centrifuge including increasing a vacuum level of a vacuum source based upon determining that said estimation of windage exceeds a preselected value of windage.

12. The method of claim 8 wherein said identifying said desired relationship is a step of establishing a relationship between temperature within said centrifuge and said estimation of windage, said controlling said centrifuge including triggering refrigeration of said centrifuge based upon determining that said estimation of windage exceeds a preselected value of windage.

13. The method of claim 8 wherein said identifying said desired relationship and said controlling said centrifuge to promote said desired relationship are performed in the absence of identifying said rotor.

14. The method of claim 8 further comprising repeating said steps of forming an estimation of windage, identifying a desired relationship and controlling said centrifuge for changes in rotational speed of said rotor.

15. A centrifuge system comprising:
drive means for rotatably supporting a centrifuge rotor within a chamber;
means for determining windage of said centrifuge rotor at a first rotational speed;
means, responsive to said means for determining windage, for estimating windage at a second rotational speed; and
means, responsive to said means for estimating, for controlling an operation parameter of said centrifuge system based upon an estimation of windage determined by said means for estimating at said second rotational speed.

16. The centrifuge system of claim 15 wherein said means for controlling includes a source of vacuum in fluid communication with said chamber.

17. The centrifuge system of claim 15 wherein said means for controlling includes a source of refrigeration operatively associated with said chamber.

18. The system of claim 15 wherein said drive means includes drive proportional and integral gain values responsive to said means for controlling.

* * * * *